United States Patent [19]

Auer

[11] Patent Number: 4,801,691

[45] Date of Patent: Jan. 31, 1989

[54] METHOD FOR REMOVING SODIUM DODECYL SULFATE FROM SODIUM DODECYL SULFATE SOLUBILIZED PROTEIN SOLUTIONS

[75] Inventor: Henry E. Auer, Skokie, Ill.

[73] Assignee: International Minerals & Chemical Corp., Terre Haute, Ind.

[21] Appl. No.: 50,146

[22] Filed: May 15, 1987

[51] Int. Cl.⁴ ............................ C07K 3/24; C07K 3/28
[52] U.S. Cl. ...................................... 530/399; 435/212; 435/226; 530/305; 530/344; 530/351; 530/380; 530/412; 530/408; 530/416; 530/417; 530/422
[58] Field of Search ............... 530/351, 399, 412, 416, 530/417, 422, 408, 305, 344, 380; 435/212, 226

[56] References Cited

U.S. PATENT DOCUMENTS

| | | | |
|---|---|---|---|
| 4,058,510 | 11/1977 | Concilio-Nolan et al. | 530/408 X |
| 4,511,502 | 4/1985 | Builder et al. | 260/112 |
| 4,511,503 | 4/1985 | Olson et al. | 260/112 |
| 4,518,526 | 5/1985 | Olson | 260/112 |
| 4,530,787 | 7/1985 | Shaked et al. | 260/112 |
| 4,569,790 | 2/1986 | Koths et al. | 260/112 |
| 4,572,798 | 2/1986 | Koths et al. | 260/112 |
| 4,620,948 | 11/1986 | Builder et al. | 530/419 |
| 4,677,196 | 6/1987 | Rausch et al. | 530/417 X |
| 4,766,224 | 8/1988 | Rausch | 530/412 |

OTHER PUBLICATIONS

Kapp et al., Removal of Sodium Dodecyl Sulfate from Proteins, Analytical Biochemistry 91, 230–235 (1978).
Putnam, The Interactions of Proteins and Synthetic Detergents, Advances in Protein Chemistry, vol. 4, 79–122(1948).

*Primary Examiner*—Howard E. Schain
*Attorney, Agent, or Firm*—Wendell R. Guffey; Thomas L. Farquer

[57] ABSTRACT

Guanidine hydrochloride (GCl) is used to remove excess sodium dodecyl sulfate (SDS) from SDS-solubilized protein solutions, and particularly from SDS-solubilized inclusion body solutions, GCl is added to the solution containing SDS to induce the formation of a GCl-SDS complex (GDS) which, when allowed to precipitate, can easily be removed by centrifugation, filtration, or other suitable means.

19 Claims, 1 Drawing Sheet

METHOD FOR REMOVING SODIUM DODECYL SULFATE FROM SODIUM DODECYL SULFATE SOLUBILIZED PROTEIN SOLUTIONS

BACKGROUND OF THE INVENTION

This invention relates generally to methods for removing sodium dodecyl sulfate (SDS) from a solution and particularly to a method using guanidine hydrochloride (GCl) to remove excess SDS from SDS-solubilized protein solutions.

Heterologous DNA segments that encode for a particular protein can be inserted into host microorganisms using recombinant DNA technology. By growing the transformant microorganisms under conditions which induce the expression of proteins, heterologous proteins such as insulin, somatotropins, interleukins, interferons, somatomedins, and the like can be produced in large quantities at a relatively low cost.

Unfortunately, heterologous proteins produced by transformant microorganisms are frequently not biologically active because they do not fold into the proper tertiary structure when transcribed within the microorganism. The heterologous proteins tend to form aggregates which are recognizable within the cell as "inclusion bodies". These inclusion bodies may also be caused by the formation of covalent intermolecular disulfide bonds which link together several protein molecules to form insoluble complexes. The inclusion bodies generally contain mostly heterologous protein and a small fraction of contaminating host microorganism proteins.

Several processes have been developed to extract the inclusion bodies from the microorganisms and convert the heterologous proteins contained therein into proteins having native bioactivity consistent with the natural parent or non-recombinant proteins. These processes generally involve disrupting the microorganism cell, separating the inclusion bodies from cell debris, solubilizing the inclusion body proteins in a denaturant/detergent which unfolds the protein, separating the heterologous inclusion body proteins from contaminating proteins, and removing the denaturant/detergent thereby allowing the heterologous proteins to refold into a bioactive tertiary conformation. These general steps may be carried out in different orders and using several different techniques, equipment, and chemicals.

Several purification schemes following this general outline have been developed: U.S. Pat. No. 4,511,502 discloses a process wherein the solubilized protein solution is passed over a molecular sieve or centrifuged to remove high molecular weight contaminating proteins. The denaturant is subsequently removed by dialysis to allow the protein to refold into its bioactive conformation. U.S. Pat. No. 4,511,503 discloses solubilizing inclusion body proteins with a strong denaturant. The strong denaturant permits the improperly folded protein molecules to unfold and become soluble in the denaturant solution. The denaturant is subsequently removed by dialysis to allow the protein to refold into a bioactive conformation.

U.S. Pat. No. 4,518,526 discloses a process wherein transformed cells are treated with a buffered solution of sufficient ionic strength to solubilize most of the whole cell protein while leaving the heterologous protein in insoluble aggregates. The transformed cells are lysed and the supernatant containing the solubilized whole cell proteins is separated from the insoluble inclusion bodies. The inclusion bodies are then solubilized using a strong denaturant.

Each of these patents deals extensively with the use of concentrated guanidine hydrochloride (GCl) as a denaturant and suggests the use of SDS as a detergent/denaturant in the process. There are, however, no methods disclosed for using SDS in recovery procedures nor for removing SDS from the protein solution to allow refolding. Presumably, SDS could be removed using dialysis and other techniques disclosed in the patent for the removal of GCl, although this is rendered less practical because of the low critical micelle concentration and large micellar size of the detergent.

Unfortunately, these techniques are often incompatible with current protein purification procedures. Also, the reagents and process conditions used during purification often induce protein reaggregation and precipitation, thus reducing the yield and increasing production costs.

Another method for recovering the heterologous protein in bioactive form comprises separating inclusion bodies from cell debris solubilizing the inclusion bodies in SDS, separating the SDS-heterologous protein complexes from those containing contaminating proteins, and removing the SDS from the heterologous protein solution using chromatography. The SDS must be added in sufficient amounts to form SDS-protein complexes. Typically an excess of SDS is added to insure complete protein solubilization. This excess, non-protein-bound SDS remains in the solution and must be removed before the protein can be restored to its bioactive conformation. As the SDS is removed the protein refolds into its bioactive tertiary structure.

Purification schemes using SDS as a denaturant/detergent generally involve solubilizing the inclusion body by adding excess SDS to denature/unfold the proteins. SDS exists in solution in two forms: (1) SDS bound to the protein in a SDS:protein complex and (2) excess, non-protein-bound SDS in solution. SDS is removed by dialysis, ion retardation chromatography, or other suitable means to allow the protein to refold into a bioactive conformation. The resulting protein is bioactive at this stage or, if not bioactive at this stage, can be further processed to produce a purified bioactive protein.

Several methods are available for the removal of SDS. Kapp et al., Anal. Biochem., 91:230–33(1978) discloses a method for removing SDS from SDS-protein solutions using ion-retardation chromatography resin AG11A8. The problem with this method is the time required to chromatograph large quantities of SDS-proten solution and the cost involved with regenerating or replacing the ion-retardation columns. The non-protein-bound SDS overloads the column and requires frequent column regeneration and replacement. The non-bound SDS could possibly be removed by "buffer exchange" or dialysis techniques but this would involve extra time-consuming and expensive steps. Weber et al., J. Biol. Chem., 246:4504–09(1971) demonstrated that SDS could be removed from aspartate transcarbamoylase by incubation in urea followed by anion-exchange chromatography.

Various methods for the removal of SDS from SDS-protein solutions, whether by dialysis, anion-exchange chromatography, ion-retardation chromatography, or other suitable means, share a common problem. The excess, non-protein-bound SDS must be removed before the protein-bound SDS can be removed. If dialysis is used to remove the excess SDS, large quantities of buffer must be dialyzed against the SDS-protein solution for long periods of time to remove the SDS. If chromatography is used, the SDS often saturates the column requiring frequent column replacement or regeneration. These problems are caused by the non-protein-bound SDS which was added in excess to insure the complete solubilization of the inclusion bodies. Less frequent column replacement or regeneration would be required and more optimal throughput of protein-containing feed solutions would result if a method were to exist for removing free or excess SDS before dissociating the bound SDS. A method is, therefore, needed for quickly and efficiently removing excess SDS from SDS-protein solutions. Such a method forms the subject of this invention.

SUMMARY OF THE INVENTION

Figure 1:
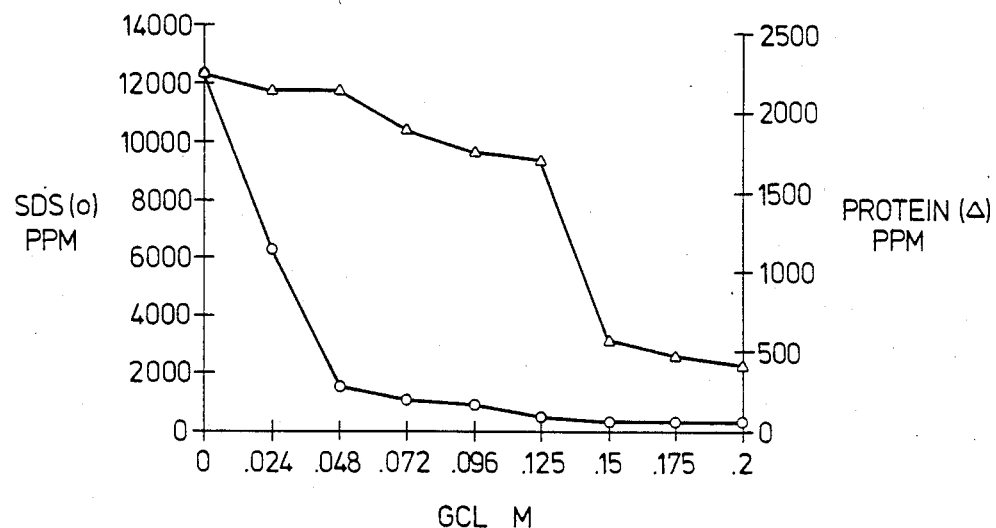
FIG. 1 is a graph showing the relationship of the total SDS content and total protein content as a function of added GCl concentration.

It is, therefore, an object of the present invention to provide a method for removing excess SDS from a SDS-solubilized protein solution.

It is another object of the present invention to provide a method for removing excess SDS from a SDS-solubilized protein solution produced from recombinant microorganism inclusion bodies.

It is another object of the present invention to provide a method for reducing the quantity of SDS in an SDS-solubilized protein solution prior to dialysis or chromatography.

It is another object of the present invention to provide a method for quickly and inexpensively removing excess SDS from SDS-solubilized protein solutions.

It is another object of the present invention to provide a method for reducing the amount of materials required and the frequency of replacement or regeneration of chromatography columns used to remove SDS from SDS-solubilized protein solutions.

These and other objects are achieved by adding guanidine hydrochloride (GCl) to a SDS-protein solution to induce the precipitation and therefore the easy removal of the excess, non-protein-bound SDS as a guanidinium-dodecyl sulfate (GDS) complex. GCl is added to the SDS solution, the solution is allowed to stand until the GDS complex precipitates, and the resulting precipitant crystals are removed from the solution, usually by centrifugation.

In the preferred embodiment, SDS-solubilized protein solutions, particularly SDS-solubilized protein solutions produced when recombinant microorganism inclusion bodies are solubilized with excess SDS, are treated with sufficient GCl to induce the precipitation of excess SDS. This treatment produces a solution containing a ratio-by-weight of SDS:protein remaining in solution of about 0.5-4.0, preferably 0.8-3.0. Under these process conditions, most of the excess, non-protein-bound SDS is removed while the solubility and bioactivity of the protein are retained. The protein-bound SDS is subsequently removed by chromatography, dialysis or other suitable means to restore the protein to its bioactive conformation.

Other objects, advantages, and novel features of the present invention will become apparent from the following detailed description of the invention.

DETAILED DESCRIPTION OF THE INVENTION

According to the present invention, a method is provided for removing SDS from a SDS-solubilized protein solution. GCl is added to the SDS-solubilized protein solution in sufficient quantities to precipitate the excess, non-protein-bound SDS as the guanidinium dodecyl sulfate (GDS) complex and the resulting precipitate is separated from the solution containing the dissolved protein.

In another aspect of the present invention, a method is provided for removing SDS from SDS-solubilized protein solutions produced from recombinant microorganism inclusion bodies. GCl is added to the SDS-solubilized protein solution in sufficient quantities to precipitate the excess SDS as the guanidinium dodecyl sulfate (GDS) complex and the resulting precipitate is separated from the solution containing the dissolved protein.

Any SDS-solubilized protein can be treated to remove excess SDS according to the present invention. Typical proteins, natural or recombinant, which may be solubilized using SDS include growth hormone release factors, somatomedins, interleukins, interferons, tissue plasminogen activators, insulins, somatotropins such as human Somatotropin, bovine Somatotropin, porcine Somatotropin and the like. As used herein, the term "recombinant proteins" refers to all proteins having native-like protein biological activity including those proteins having deleted, altered, substituted, or otherwise modified sequences.

Generally, GCl is added to a SDS-protein solution in sufficient quantities to produce a molar ratio of GCl to non-protein-bound SDS of about 1-5, preferably about 2.0-3.0. However, the amount of GCl needed to remove the excess SDS from a SDS-solubilized protein solution may vary depending upon the relative proportions of protein and SDS present originally. As a general guideline, GCl is added to the SDS-protein solution in sufficient quantities to produce a ratio-by-weight of SDS:protein remaining in solution of about 0.5-4.0, preferably 0.8-3.0. When SDS-protein solutions contain from about 0.05-5% SDS, the GCl should be added to produce from about a 0.02 to about a 0.25M GCl solution. Under these conditions, the protein will remain in solution as a monomeric molecule while the SDS precipitates and can be easily separated from the solution. Addition of excess GCl, i.e., amounts that lower the ratio-by-weight of SDS:protein remaining in solution below about 0.5, may cause proteins to rapidly form aggregates. This is presumably due to the formation of intermolecular disulfide bonds if the heterologous protein in the inclusion bodies contains free cysteinyl residues. Adding GCl such that the molar ratio of GCl:SDS is between about 1-5, preferably 2-3, is sufficient when the protein or inclusion body is dissolved in a SDS solution having a concentration of from about 0.05-5%, preferably 0.1-2%.

According to the present invention, the GDS precipitate can be removed by any method suitable for removing precipitates from a solution. Centrifugation, filtration, decantation, and the like are suitable, with centrifugation being preferred because of its simplicity and effectiveness.

The method of the present invention is particularly useful when used in conjunction with a second SDS removal technique such as dialysis, ion retardation chromatography, or the like which removes the protein-bound SDS from a protein solution. The method of the present invention removes most, greater than 98%, of the excess non-protein-bound SDS. The second technique may then be used to remove the remaining SDS, particularly the protein-bound SDS. Removing excess SDS by the method of the present invention lowers the cost and saves the time involved in removing excess SDS compared to that which would be incurred using other techniques. In particular, the present invention saves the cost of regenerating or replacing ion retardation columns and reduces the amount and therefore the cost of chemicals used in dialysis. The time devoted to column regeneration or to dialysis is also saved.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Duplicate 5 ml aliquots of a 1% solution of SDS (0.035M) in 60 mM ethanolamine buffer pH 9.0 (EA) were titrated by the addition of aliquots of 1M GCl in EA. The precipitate which formed was centrifuged to the bottom of a conical 12 ml centrifuge tube. The height of the pellet was approximated with a ruler; the volume of precipitate is roughly proportional to the cube of this value. The appearance of the solution immediately after adding the GCl was also noted. The results are shown in Table 1.

Referring to Table 1, the results show that the equivalence point occurs at a molar ratio of added GCl:SDS of approximately 2.6.

EXAMPLE 2

An experiment similar to that of Example 1 was carried out, except that 2 mg/ml recombinant bovine Somatotropin was included in the samples. The purpose was to determine whether SDS and protein could be separated from one another upon precipitation by GCl. Aliquots of 1.0M GCl were added to duplicate 5 ml portions of solution containing 1% SDS in EA. The preipitate was collected and measured as in Example 1. The depletion of rbST was determined by measuring $OD_{280}$ values on the supernatant solutions. The results for each of the two replicates are shown in Table 2.

Referring to Table 2, SDS precipitated as above with a sharp equivalence point at a molar ratio of GCl:SDS of about 2.3 with about 83% of the rbST remaining in solution. The protein precipitated nearly completely at a total GCl:SDS ratio of about 4.3. This experiment indicates that GCl precipitates free SDS from a protein-SDS mixture, leaving the protein in solution (as a protein-SDS complex) over a relatively broad window of added GCl concentrations.

EXAMPLE 3

In order to assess the concentration of SDS remaining in solution at the equivalence point after precipitation with GCl, a titration of crystal formation was carried out, using visual inspection to detect the presence of crystals. 1.00 ml samples of SDS with progressively lower concentrations were prepared in 60 mM ethanolamine buffer pH 8.9, and aliquots of 1.05M GCl were added to each. The addition of 0.100 ml corresponds to a GCl:SDS molar ratio of 3.0. After 15–30 minutes the presence or absence of crystals of precipitate was ascertained visually. The results are shown in Table 3.

Referring to Table 3, the data show that at a molar ratio of GCl:SDS=3.0, at least 98% of the free SDS in a 1% solution is precipitated by GCl under these conditions.

EXAMPLE 4

4 g of inclusion bodies containing recombinant porcine Somatotropin (rpST) were extracted with 200 mL 1% SDS in 60 mM ethanolamine buffer, pH 9, and dialyzed over a weekend to partially remove free SDS. Incremental addition of GCl was carried out up to about 0.17M. Assays for SDS and for protein were performed and selected supernatants were examined by FPLC on Superose 12. The results are shown in Table 4.

Referring to Table 4, free SDS is precipitated in accordance with the method of this invention, attaining an equivalence point represented by total SDS=0.07%, total protein=2.95 mg/ml (approximately 87% of the starting concentration). Thus most of the protein is retained in the supernatant, and not lost in the initial SDS precipitate. The SDS content, which is higher than that determined at the equivalence point in the absence of protein, represents the protein-bound SDS. Since the starting SDS concentration in this experiment was about 0.25–0.3%, less GCl was needed to precipitate the free SDS than if the starting concentration had been higher. Upon increasing the GCl concentration in this experiment to 0.17M, essentially all the protein precipitated.

EXAMPLE 5

1 g of inclusion bodies containing rpST was extracted with 200 mL 0.25% SDS in 0.1M carbonate pH 10.0. Fewer incremental additions were done, with the final GCl concentration again being 0.17M. Reducing SDS-PAGE was done on selected fractions. The reducing SDS-PAGE results confirm the absence of protein in the SDS precipitate, and the presence of rpST in the supernatant.

EXAMPLE 6

GCl Precipitation of SDS and Protein in

Inclusion Body Complexes

In order to determine the fate of SDS and of protein according to the method of this invention, GCl precipitation of solubilized inclusion bodies was examined. Inclusions containing rpST were dissolved overnight in 1% SDS, 60 mM ethanolamine pH 9.0, 5 mM EDTA. Additions of GCl were then made, and precipitates removed by centrifugation. Careful attention was paid to excluding atmospheric oxygen during incubations and centrifugations at each stage, by purging with nitrogen. The objective was to determine the content of SDS and of total protein at each incremental addition of GCl. Protein concentrations were determined by the BCA method (Pierce Chemical Co.) and SDS was determined by the acridine orange assay (R. L. Sokoloff and R. P. Frigon, *Analytical Biochemistry*, Vol. 118, p138–41 (1981)).

FIG. 1 presents the dependence of the total SDS content and the total protein content as a function of added GCl concentration. The results indicate that free SDS is precipitated at quite low amounts of added GCl, while the protein content remains essentially unchanged during the process of SDS precipitation. The majority of the protein is not precipitated until considerably higher GCl concentrations are attained.

Figure 2:
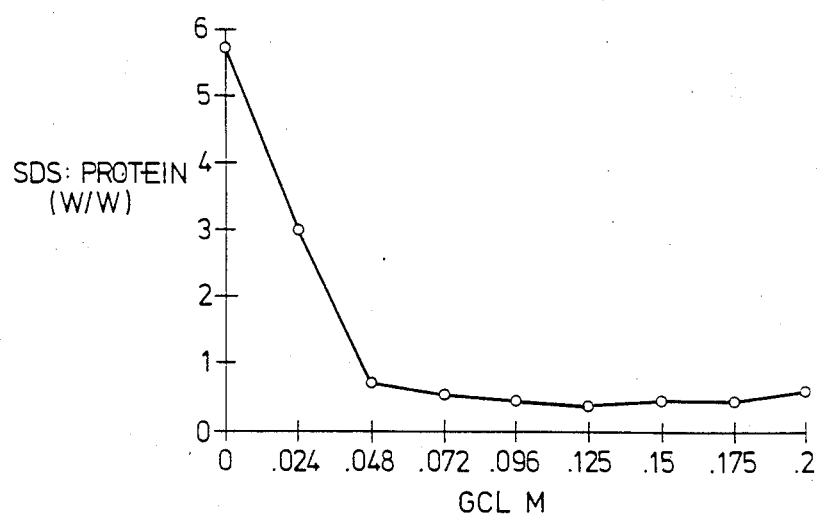
FIG. 2 is a graph showing the SDS:Protein ratio as a function of GCl concentration, using the data presented in FIG. 1.

FIG. 2 presents the SDS:protein ratio as a function of GCl concentration added for the same experiment as that shown in FIG. 1. This graph shows conclusively that after the free SDS is precipitated by the GCl, the SDS:protein ratio persists at a constant low level, about 0.4–0.5 g SDS/g protein, throughout the remainder of the GCl titration. This ratio is far lower than the value of 1.4 g SDS/g protein generally assumed to prevail under conditions of, for example, SDS-PAGE. Thus, it is concluded that this represents an SDS complex of proteins with only tightly bound SDS remaining.

Obviously many modifications and variations of the present invention are possible in light of the above teachings. It is therefore to be understood that within the scope of the appendd claims the invention may be practiced otherwise than as specifically described.

TABLE 1

| Added [GCl], M | Molar Ratio GCl:SDS | Height of Precipitate, cm | Appearance of Solution |
|---|---|---|---|
| 0.040 | 1.2 | 1.1 / 1.3 | Thick ppt. |
| 0.080 | 2.3 | 1.8 / 1.8 | Thick ppt. |
| 0.120 | 3.5 | 1.9 / 2.0 | Faintly cloudy |
| 0.140 | 4.0 | 1.9 / 2.0 | Clear |

TABLE 2

| Added [GCl], M | Molar Ratio GCl:SDS | Height of Precipitate, cm | | $OD_{280}$ | |
|---|---|---|---|---|---|
| 0 | 0 | | | 0.886 | 0.829 |
| 0.06 | 1.7 | 1.6 | 1.6 | 0.798 | 0.754 |
| 0.07 | 2.0 | 1.6 | 1.5 | 0.779 | 0.737 |
| 0.08 | 2.3 | 1.8 | 1.8 | 0.736 | 0.692 |
| 0.09 | 2.6 | 1.8 | 1.8 | 0.703 | 0.655 |
| 0.10 | 2.9 | 1.8 | 1.8 | 0.673 | 0.621 |
| 0.12 | 3.5 | 1.8 | 1.8 | 0.639 | 0.571 |
| 0.13 | 3.7 | 1.8 | 1.8 | 0.594 | 0.567 |
| 0.14 | 4.0 | 1.8 | 1.8 | 0.747* | 0.709* |
| 0.15 | 4.3 | 1.8 | 1.8 | 0.313* | 0.572* |
| 0.16 | 4.6 | | | 0.199 | 0.195 |
| 0.17 | 4.9 | | | 0.115 | 0.112 |

*These solutions were turbid even after centrifugation, so that the absorbance values contain contributions from light scattering in addition to the intrinsic absorption from the remaining protein.

TABLE 3

| [SDS], % (wt/vol) | Vol. of 1.05 M GCl, ml | Precipitate |
|---|---|---|
| 1.00 | 0.100 | Yes |
| 0.20 | 0.100 | Yes |
| 0.10 | 0.100 | Yes |
| 0.05 | 0.100 | Yes |
| 0.02 | 0.100 | Yes |
| 0.01 | 0.100 | No |
| 0.01 | 0.200 | Yes |

TABLE 4

| [GCl], M | Total [SDS], % (wt/vol) | Protein in Supnt., mg/ml |
|---|---|---|
| 0.014 | 0.31 | 3.40 |
| 0.028 | 0.22 | 3.30 |
| 0.042 | 0.12 | 3.00 |
| 0.056 | 0.071 | 2.95 |
| 0.096 | 0.062 | 2.85 |

TABLE 4-continued

| [GCl], M | Total [SDS], % (wt/vol) | Protein in Supnt., mg/ml |
|---|---|---|
| 0.125 | | 2.55 |

What is claimed is:

1. A method for removing excess sodium dodecyl sulfate (SDS) from a SDS-solubilized protein solution, comprising:
   adding guanidine hydrochloride (GCl) in amounts sufficient to produce a GCl:SDS molar ratio of between about 1 to 5 to the solution to induce SDS precipitation;
   allowing the excess SDS to precipitate as the guanidinum dodecyl sulfate (GDS) complex; and
   removing the GDS precipitate from the solution.

2. The method of claim 1 wherein the GCl is added in amounts sufficient to produce a molar ratio of GCl to non-protein-bound SDS of between about 2.0 to 3.0.

3. The method oc claim 1 wherein GCl is added in amounts sufficient to produce a ratio-by-weight of SDS:protein remaining in solution of about 0.5–4.0.

4. The method of claim 1 wherein GCl is added in amounts sufficient to produce a ratio-by-weight of SDS:protein remaining in solution of about 0.8–3.0.

5. The method of claim 1 wherein the protein solution has a SDS concentration of from about 0.05–5%.

6. The method of claim 1 wherein the protein solution has a SDS concentration of from about 0.1–2%.

7. The method of claim 1 wherein the solubilized protein is selected from the group consisting of growth hormone release factors, somatomedins, interleukins, interferons, tissue plasminogen activators and insulins.

8. The method of claim 1 wherein the solubilized protein is a somatotropin.

9. The method of claim 1 wherein the protein solution is a SDS-solubilized protein solution produced from recombinant microorganism inclusion bodies.

10. The method of claim 9 wherein the solubilized protein is selected from the group consisting of growth hormone release factors, somatomedins, interleukins, interferons, tissue plasminogen activators, and insulins.

11. The method of claim 9 wherein the solubilized protein is a somatotropin.

12. A method for removing excess SDS from a SDS-solubilized protein solution produced from recombinant microorganism inclusion bodies, comprising:
   adding guanidine hydrochloride (GCl) in amounts sufficient to produce a GCl:SDS molar ratio of between about 1 to 5 to the solution to induce SDS precipitation;
   allowing the excess SDS to precipitate as the guanidinium doecyl sulfate (GDS) complex; and
   removing the GDS precipitate from the solution.

13. The method of claim 12 wherein the GCl is added in amounts sufficient to produce a molar ratio of GCl to non-protein-bound SDS of between about 2.0 to 3.0.

14. The method of claim 12 wherein GCl is added in amounts sufficient to produce a ratio-by-weight of SDS:protein remaining in solution of about 0.5–4.0.

15. The method of claim 12 wherein GCl is added in amounts sufficient to produce a ratio-by-weight of SDS:protein remaining in solution of about 0.8–3.0.

16. The method of claim 12 wherein the protein solution has a SDS concentration of from about 0.05–5%.

17. The method of claim 12 wherein the protein solution has a SDS concentration of from about 0.1–2%.

18. The method of claim 12 wherein the solubilzed protein is selected from the group consisting of growth hormone release factors, somatomedins, interleukins, interferons, tissue plasminogen activators, and insulins.

19. The method of claim 12 wherein the solubilized protein is a somatotropin.

* * * * *

UNITED STATES PATENT AND TRADEMARK OFFICE
CERTIFICATE OF CORRECTION

PATENT NO. : 4,801,691
DATED : January 31, 1989
INVENTOR(S) : Henry E. Auer

It is certified that error appears in the above-identified patent and that said Letters Patent is hereby corrected as shown below:

Column 2, line 52, "proten" should read --protein--
Column 3, line 17, following the word invention, delete --cl--
Column 5, line 49, "preipitate" should read --precipitate--
Column 7, line 22, "appendd" should read --appended--
Column 8, lines 14-15, Claim 1, "guanidinum" should read --guanidinium--
Column 8, line 19, Claim 3, "oc" should read --of--
Column 8, line 49, Claim 12, "doecyl" should read --dodecyl--
Column 8, line 63, Claim 18, "solubilzed" should read --solubilized--

Signed and Sealed this

Seventeenth Day of April, 1990

Attest:

HARRY F. MANBECK, JR.

*Attesting Officer*   *Commissioner of Patents and Trademarks*